United States Patent
Schafer et al.

(10) Patent No.: US 10,977,792 B2
(45) Date of Patent: Apr. 13, 2021

(54) QUANTITATIVE EVALUATION OF TIME-VARYING DATA

(71) Applicant: Siemens Healthcare GmbH, Erlangen (DE)

(72) Inventors: Sebastian Schafer, Madison, WI (US); Markus Kowarschik, Nuremberg (DE); Sonja Gehrisch, Nuremberg (DE); Kevin Royalty, Fitchburg, WI (US); Christopher Rohkohl, Brixen im Thale (AT)

(73) Assignee: Siemens Healthcare GmbH, Erlangen (DE)

(*) Notice: Subject to any disclaimer, the term of this patent is extended or adjusted under 35 U.S.C. 154(b) by 58 days.

(21) Appl. No.: 16/486,944

(22) PCT Filed: Feb. 23, 2018

(86) PCT No.: PCT/US2018/019315
§ 371 (c)(1),
(2) Date: Aug. 19, 2019

(87) PCT Pub. No.: WO2018/186943
PCT Pub. Date: Oct. 11, 2018

(65) Prior Publication Data
US 2020/0193590 A1 Jun. 18, 2020

Related U.S. Application Data

(60) Provisional application No. 62/482,080, filed on Apr. 5, 2017.

(51) Int. Cl.
*G06K 9/00* (2006.01)
*G06T 7/00* (2017.01)
(Continued)

(52) U.S. Cl.
CPC ......... *G06T 7/0012* (2013.01); *A61B 5/0263* (2013.01); *A61B 6/507* (2013.01);
(Continued)

(58) Field of Classification Search
None
See application file for complete search history.

(56) References Cited

U.S. PATENT DOCUMENTS 9,095,313 B2 * 8/2015 Tolkowsky .......... A61B 5/0066
2003/0004405 A1 1/2003 Townsend et al.
(Continued)

FOREIGN PATENT DOCUMENTS

EP 3087921 A1 11/2016
JP S58019236 A 2/1983
(Continued)

OTHER PUBLICATIONS

Barfett, Joseph John et al.: "Intra-vascular blood velocity and volumetric flow rate calculated from dynamic 4D CT angiography using a time of flight technique", International Journal of Cardiovascular Imaging, Kluwer Academic Publishers, Dordrecht, NL, vol. 30, No. 7, Jul. 8, 2014 (Jul. 8, 2014), pp. 1383-1392.

*Primary Examiner* — Atiba O Fitzpatrick

(57) ABSTRACT

A framework for quantitative evaluation of time-varying data. In accordance with one aspect, the framework delineates a volume of interest in a four-dimensional (4D) Digital Subtraction Angiography (DSA) dataset (204). The framework then extracts a centerline of the volume of interest (206). In response to receiving one or more user-selected points along the centerline (208), the framework determines at least one blood dynamics measure associated with the one or more user-selected points (210), and generates a visualization based on the blood dynamics measure (212).

20 Claims, 9 Drawing Sheets

(51) Int. Cl.
*G06T 7/11* (2017.01)
*G06T 7/66* (2017.01)
*A61B 5/026* (2006.01)
*A61B 6/00* (2006.01)
*A61B 8/06* (2006.01)

(52) U.S. Cl.
CPC ................. *A61B 8/06* (2013.01); *G06T 7/11* (2017.01); *G06T 7/66* (2017.01); *G06T 2200/24* (2013.01); *G06T 2207/10076* (2013.01); *G06T 2207/20224* (2013.01); *G06T 2207/30104* (2013.01); *G06T 2207/30172* (2013.01)

(56) References Cited

U.S. PATENT DOCUMENTS

| | | | |
|---|---|---|---|
| 2008/0187199 A1* | 8/2008 | Gulsun | G06T 7/149 382/131 |
| 2010/0004526 A1* | 1/2010 | Wei | A61P 25/28 600/407 |
| 2014/0270436 A1* | 9/2014 | Dascal | A61B 6/463 382/130 |
| 2015/0223703 A1* | 8/2015 | Abd-Elmoniem | A61B 5/055 600/413 |
| 2020/0345321 A1* | 11/2020 | Tolkowsky | A61B 6/541 |

FOREIGN PATENT DOCUMENTS

| | | |
|---|---|---|
| JP | S62030493 A | 2/1987 |
| JP | H04208138 A | 7/1992 |
| JP | 2010154982 A | 7/2010 |
| JP | 2013010005 A | 9/2014 |
| JP | 2015097724 A | 5/2015 |
| WO | 2017039646 A1 | 3/2017 |

* cited by examiner

QUANTITATIVE EVALUATION OF TIME-VARYING DATA

TECHNICAL FIELD

The present disclosure generally relates to data processing, and more particularly to quantitative evaluation of time-varying data.

BACKGROUND

Angiography is a common method used to represent blood vessels based on diagnostic imaging methods, such as X-ray or Magnetic Resonance Tomography (MRT). For an improved representation of the vessels under examination, Digital Subtraction Angiography (DSA) has been developed. DSA is an angiography technique used in interventional radiology to clearly visualize blood vessels in a bony or dense soft tissue environment. Images are produced by subtracting a 'pre-contrast image' or the mask from subsequent images acquired after the contrast medium has been introduced into a structure or tissue of interest. These images can be used to provide time-resolved or time-varying information that shows the development of the structure or tissue of interest over time.

In current clinical practice, time-resolved information is generally only available in two dimensions. Typically, the surgeon has to perform a two-dimensional (2D) to three-dimensional (3D) mental conversion from the 2D projection images to 3D anatomy in order to assess and diagnose vascular pathologies and blood flow abnormalities. The filling of the vasculature changes from frame to frame, leaving the surgeon with the difficult task of interpreting 3D filling from varying 2D snapshots. Regardless of acquisition/viewing angle, vessel segments that are overlapping and/or obscured may therefore be compromised, leading to potentially missing image information or incorrect diagnosis. Problems include, for example, vessel overlap or vessels running orthogonal to the detector plane.

Recent years have seen the introduction of methodologies for 3D DSA. In one method, a mask projection image sequence is first acquired during a rotational scan of the angiographic device, followed by a sequence of rotational fill projection images acquired after the introduction of contrast agent. The mask projection images are subtracted from the fill projection images to generate projection image data that displays a subject's vascular anatomy acquired at different viewing angles. Using 3D reconstruction techniques, a volumetric DSA dataset of a subject's vasculature can be created. Alternatively, a reconstructed mask volume can be subtracted from a reconstructed (contrast-enhanced) fill volume in order to generate a 3D DSA.

The last years have seen the introduction of a reconstruction method called 4D DSA that is aimed at reproducing the contrast dynamics visible in the projection images in a 3D volume, effectively creating a time-resolved 3D dataset. Methods for reconstructing datasets derived from a single C-Arm system have been formulated.

SUMMARY

Described herein is a framework for quantitative evaluation of time-varying data. In accordance with one aspect, the framework delineates a volume of interest in a four-dimensional (4D) Digital Subtraction Angiography (DSA) dataset. The framework then extracts a centerline of the volume of interest. In response to receiving one or more user-selected points along the centerline, the framework determines at least one blood dynamics measure associated with the one or more user-selected points, and generates a visualization based on the blood dynamics measure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
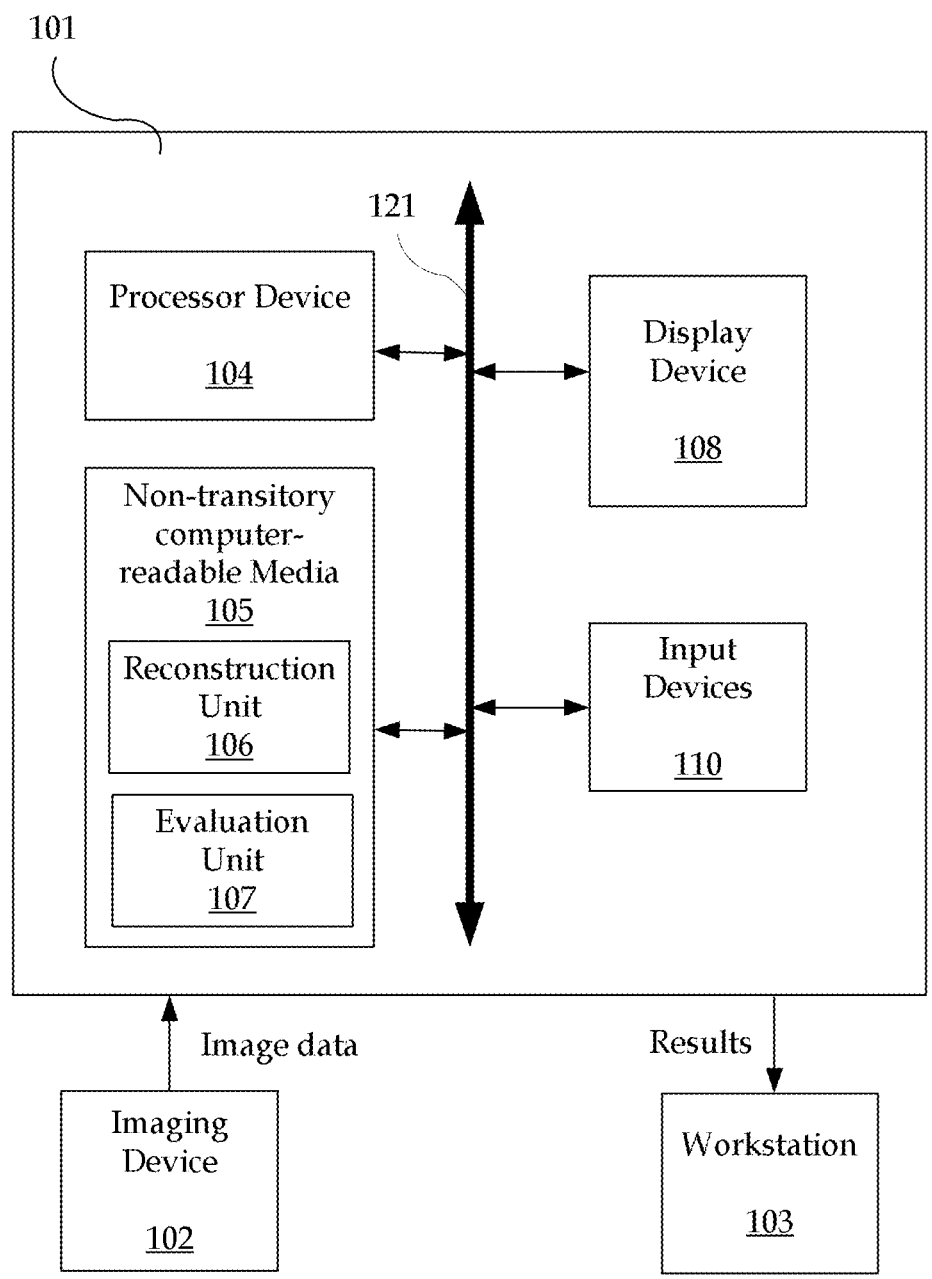
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images, voxels for 3D images, dynamic voxels or doxels for 4D datasets). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture, 3D volume or 4D dataset. For a 2- or 3-Dimensional image, the domain of the image is typically a 2- or 3-Dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, "voxels" for volume image elements, often used with respect to 3D imaging, and "doxels" for 4D datasets can be used interchangeably. It should be noted that the 3D volume image and the time-resolved 4D volume image are themselves synthesized from image data obtained as pixels on a 2D sensor array and displayed as a 2D image from some angle of view. Thus, 2D image processing and image analysis techniques can be applied to the 3D volume image data. In the description that follows, techniques described as operating upon doxels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel", "subject voxel" and "subject doxel" are used to indicate a particular image element as it is operated upon using techniques described herein.

One aspect of the present framework facilitates quantitative evaluation of a four-dimensional (4D) Digital Subtraction Angiography (DSA) dataset. A 4D dataset generally refers to a time-resolved three-dimensional (3D) dataset. The 4D DSA dataset may be derived from a pair of rotational acquisitions: a rotational mask run that generates mask projection image data followed by a rotational contrast-enhanced fill run that generates fill projection image data. The temporal dynamics contained in the projection image data may be functionally encoded into static 3D-DSA constraining image data to generate the 4D DSA dataset. In its traditional form, 4D DSA is only a qualitative tool used for visual inspection. Nevertheless, the incorporated contrast dynamics allow for assessing quantitative metrics, such as blood flow velocity or volumetric flow rate.

In some implementations, the present framework extracts one or more quantitative measures from an existing 4D DSA dataset. The framework may then determine a differential volumetric flow rate at a user-selected point or volumetric flow rate between two user-selected points in a volume of interest. Additionally, a reliability guide in the form of vessel straightness may also be provided to aid the user in interpreting the results.

FIG. 1 is a block diagram illustrating an exemplary system 100. The system 100 includes a computer system 101 for implementing the framework as described herein. Computer system 101 may be a desktop personal computer, a portable laptop computer, another portable device, a mini-computer, a mainframe computer, a server, a cloud infrastructure, a storage system, a dedicated digital appliance, a communication device, or another device having a storage sub-system configured to store a collection of digital data items. In some implementations, computer system 101 operates as a standalone device. In other implementations, computer system 101 may be connected (e.g., using a network) to other machines, such as imaging device 102 and workstation 103. In a networked deployment, computer system 101 may operate in the capacity of a server (e.g., thin-client server, such as Syngo®.via by Siemens Healthcare), a user machine in server-client user network environment, or as a peer machine in a peer-to-peer (or distributed) network environment.

Computer system 101 may include a processor device or central processing unit (CPU) 104 coupled to one or more non-transitory computer-readable media 105 (e.g., computer storage or memory), display device 108 (e.g., monitor) and various input devices 110 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 105. In particular, the present techniques may be implemented by a reconstruction unit 106 and an evaluation unit 107. Non-transitory computer-readable media 105 may include random access memory (RAM), read-only memory (ROM), magnetic floppy disk, flash memory, and other types of memories, or a combination thereof. The computer-readable program code is executed by processor device 104 to process images or image data acquired by, for example, imaging device 102. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing image datasets, dynamic reconstruction instructions, knowledge base, and so forth. Such data may also be stored in external storage or other memories. The external storage may be implemented using a database management system (DBMS) managed by the processor device 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The imaging device 102 may be a radiology scanner, such as a single or dual C-arm angiographic X-ray system for acquiring DSA image data. The workstation 103 may include a computer and appropriate peripherals, such as a keyboard and display device, and can be operated in conjunction with the entire system 100. For example, the workstation 103 may communicate with the imaging device 102 so that the image data collected by the imaging device 102 can be rendered at the workstation 103 and viewed on a display device. The imaging device 102 may also be connected to third-party devices or systems, such as a hemodynamic recording system.

The workstation 103 may communicate directly with the computer system 101 to display processed data and/or output image processing results (e.g., 4D DSA dataset). The workstation 103 may include a graphical user interface to receive user input via an input device (e.g., keyboard, mouse, touch screen, voice or video recognition interface, etc.) to manipulate visualization and/or processing of data. For example, the user may view the processed image data, and specify one or more view adjustments or preferences (e.g., zooming, cropping, panning, rotating, changing contrast, changing color, changing view angle, changing view depth, changing rendering or reconstruction technique, etc.), navigate to a particular region of interest by specifying a "goto" location, navigate (e.g., stop, play, step through, etc.) temporal volumes of the reconstructed 4D dataset, and so forth.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
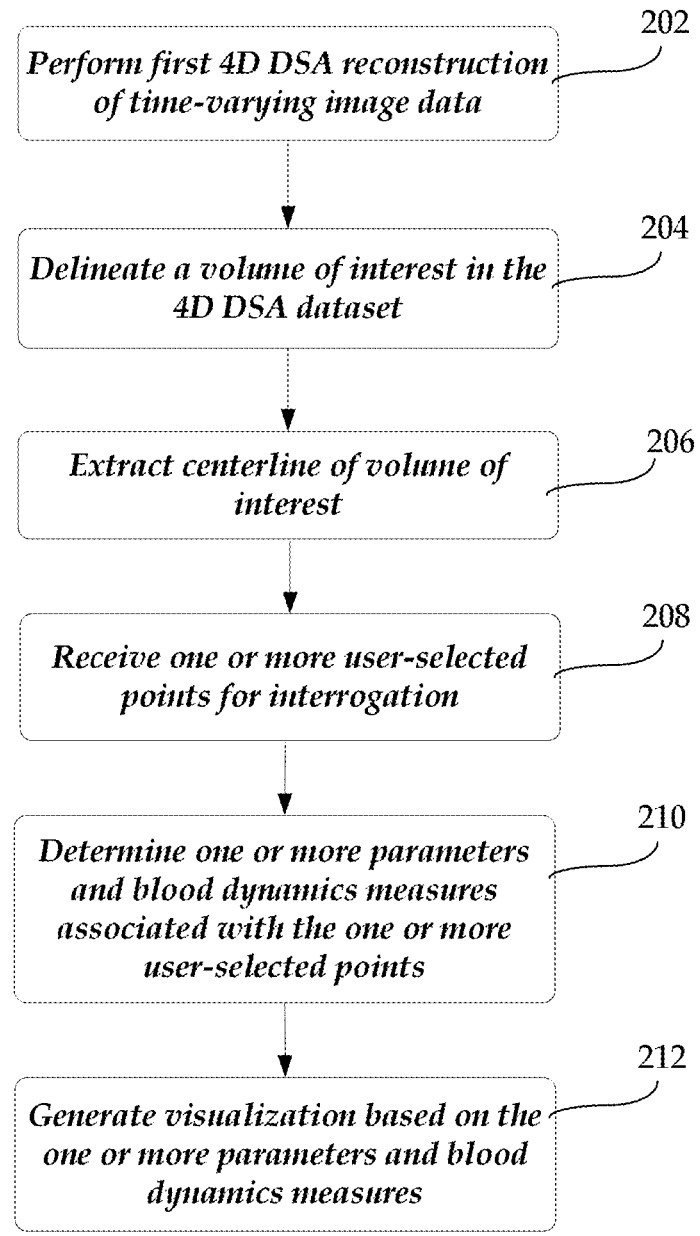
FIG. 2 shows an exemplary method of quantitative evaluation performed by a computer system.

FIG. 2 shows an exemplary method 200 of quantitative evaluation performed by a computer system. It should be understood that the steps of the method 200 may be performed in the order shown or a different order. Additional, different, or fewer steps may also be provided. Further, the method 200 may be implemented with the system 101 of FIG. 1, a different system, or a combination thereof.

At 202, reconstruction unit 106 performs a first 4D reconstruction of time-varying image data to generate a 4D (or time-varying 3D) DSA image dataset V(t) of an object of interest. Each dynamic voxel (or doxel) of the 4D DSA image dataset V(t) represents the injected contrast flow in the vasculature of the object of interest at a particular three-dimensional location and at a particular time. The object of interest may be any biological object identified for investigation or examination, such as a portion of a patient's or subject's brain, heart, leg, arm, and so forth. The object of interest includes one or more vessel structures (e.g., blood vessels, arteries, vascular tree or network, etc.). The one or more vessel structures may be dynamic or time-varying structures that can be filled with a contrast agent or medium for observing its propagation over time. In some implementations, a static (i.e., non-temporal) 3D image data of a device (e.g., coil package, stent, flow diverting device) implanted in the object of interest is also reconstructed.

The time-varying data may be a set of 2D projection images that are acquired by performing a rotational scan or angular acquisitions using imaging device 102. A single mask and fill acquisition may be performed via the imaging device 102. More particularly, a mask image dataset may first be acquired via the imaging device 102 such that it can be subtracted from the corresponding time-varying contrast filled projection image dataset. A mask image is simply an image of the same area before the contrast agent (or medium) is administered to fill the vessel-like structures of the irradiated object of interest that is to be investigated. The actual angular- and time-varying 2D projection data may be based on a contrast enhanced acquisition that is initiated before or after the injection of X-ray contrast medium into the vessel-like structures as the first inflow of contrast becomes visible. Both mask and fill runs may follow the same acquisition trajectory. The trajectory may cover the entire field-of-view (FOV) range of a 3D DSA.

Imaging device 102 may be a scanner or C-arm system with a single imaging plane or multiple (e.g., dual) imaging planes. For example, imaging device 102 may be a flat-panel based X-ray scanner that includes at least one pair of X-ray source and X-ray detector. Alternatively, imaging device 102 may include a rotating CT gantry covering at least one pair of X-ray source and X-ray detector. In other implementations, imaging device 102 is an MR scanner. In yet other implementations, imaging device 102 is a rotating optical CT gantry covering at least one pair of light source and optical detector. Other types of imaging device 102, such as angular sampling ultrasound, may also be used.

Figure 3A:
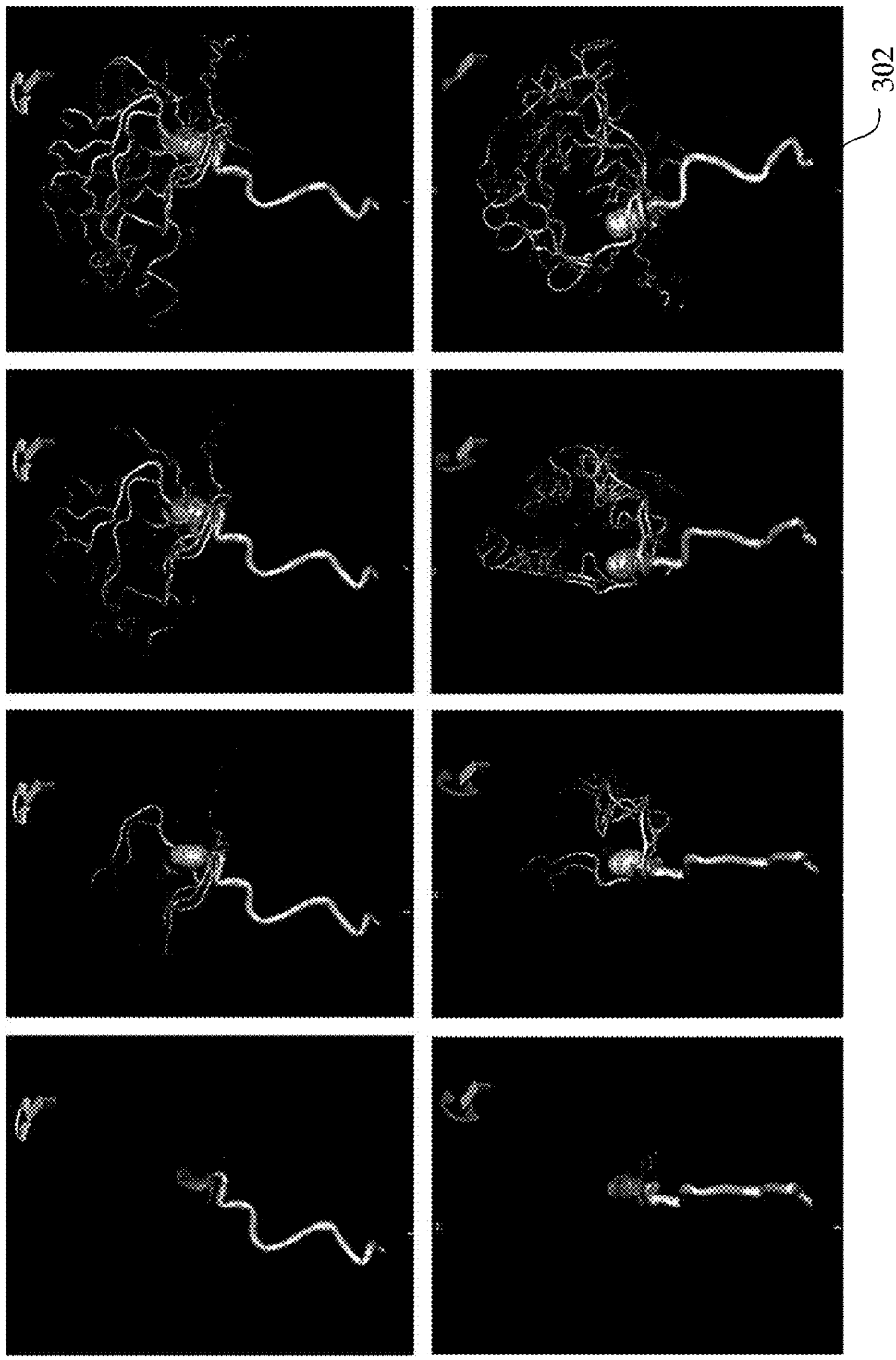
FIG. 3a shows a time series of three-dimensional (3D) angiographic images of a patient's brain that were reconstructed using a single rotating imaging plane.

FIG. 3a shows a time series of 3D angiographic images 302 of a patient's brain that were reconstructed using a single rotating imaging plane. Methods for performing a 4D DSA reconstruction of time-varying image data acquired by a single rotating plane C-arm system are described in application Ser. No. 14/302,596 filed on Jun. 12, 2014 (now U.S. Pub. No. 2014/0376791), which is hereby incorporated by reference. These methods may determine time-varying volumetric attenuation curves of the vessel-like structures of interest, resulting in a 3D plus time (or 4D DSA) volumetric dataset that includes the time dimension. The 4D DSA dataset may also be derived from time- and projection angle-varying data. Confidence values or curves may be used in performing interpolation of time-resolved 3D DSA. Such framework may be applied once, or in an iterative fashion. The 4D DSA dataset may also be dynamically and iteratively reconstructed based on, for example, an initial time-varying 3D dataset derived from time-varying 2D projection data acquired at multiple angles.

Methods for performing a 4D DSA reconstruction of time-varying image data acquired by a dual C-arm system are described in German application no. 102015224176.9 filed on Dec. 3, 2015 entitled "Tomography system and method for generating a sequence of volume images of a vasculature" (also PCT application no. PCT/EP2015/079102 filed on Dec. 9, 2015), which are hereby incorporated by reference. These techniques are based on an angiographic biplane system that comprises two simultaneously rotating planes. The accuracy of the reconstructed series of time-resolved volumes can be significantly improved, since information from the two planes can be exploited to mitigate accuracy issues due to vascular overlap.

Returning to FIG. 2, at 204, evaluation unit 107 delineates (or segments) a volume of interest (VOI) in the resulting 4D DSA dataset generated by reconstruction unit 106. The volume of interest may be any vascular segment in the 4D DSA dataset that is identified for further study. The VOI may be automatically, semi-automatically or manually identified. Automatic delineation includes performing, for example, thresholding or other segmentation techniques.

In some implementations, volume-of-interest (VOI) segmentation is initiated and controlled by user selections from a user interface (e.g., vessel analysis tool) presented at workstation 103. The user interface may first load and render the 4D DSA image data for viewing by the user. The time component of the 4D DSA image data may be displayed as, for example, an aggregate of the time-frames, a color rendering or time-steps generated during interaction. The user interface may provide various user interface elements (e.g., buttons, text functions) to enable the user to select, zoom in and/or crop the volume of interest in the 4D DSA image data. The user interface may further provide a user interface element (e.g., icon) to enable the user to initiate automatic segmentation of the volume of interest through volume thresholding and point selection.

Figure 3B:
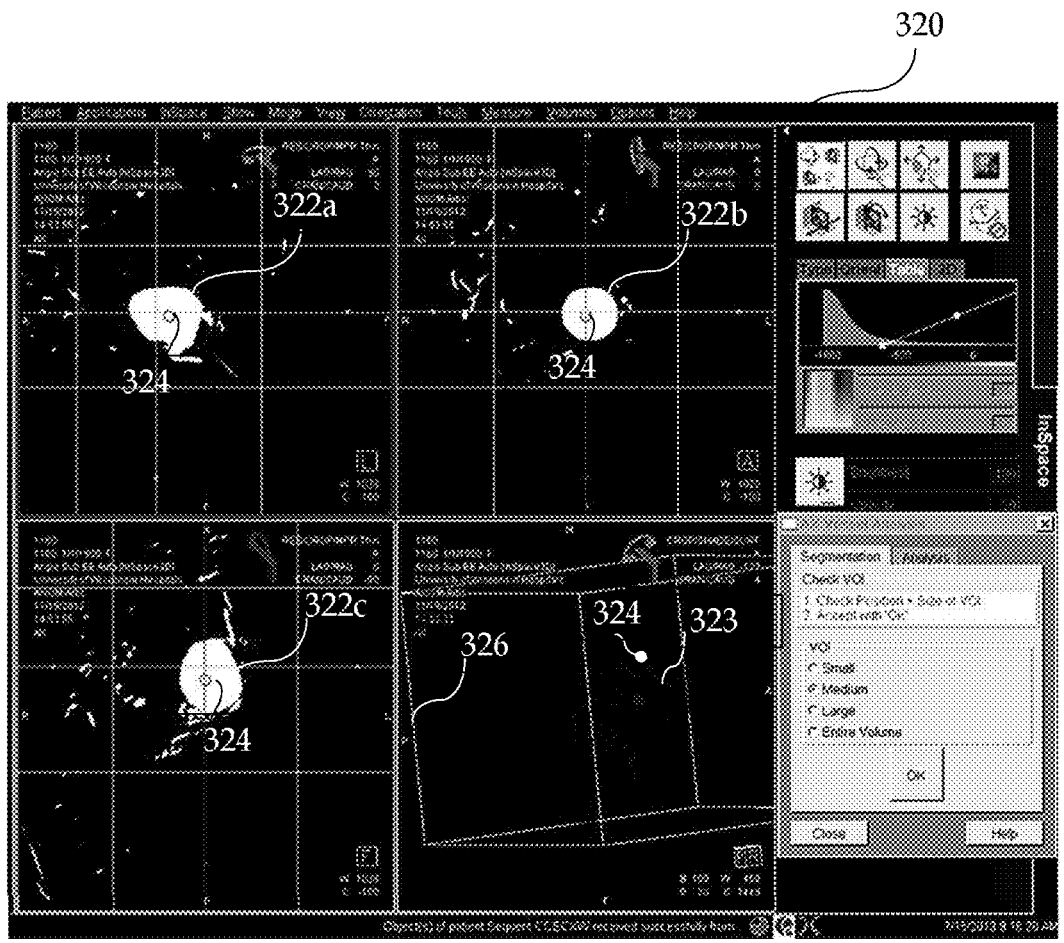
FIG. 3b shows an exemplary user interface for positioning a seed point for aneurysm evaluation.

FIG. 3b shows an exemplary user interface 320 for positioning a seed point for aneurysm evaluation. The user interface 320 displays three different slices 322a-c and a volume rendering 323 of an aneurysm (or volume of interest). The segmentation of the aneurysm is outlined by a white box 326, with a dot 324 in the center of the box 326. The dot 324 may be moved by the user to be the center of the aneurysm. The user may also change the size of the segmentation box 326 by, for example, selecting and dragging a corner of the box. The user may further adjust control parameters, such as the threshold for segmentation to include more or less structures in the segmentation.

Figure 3C:
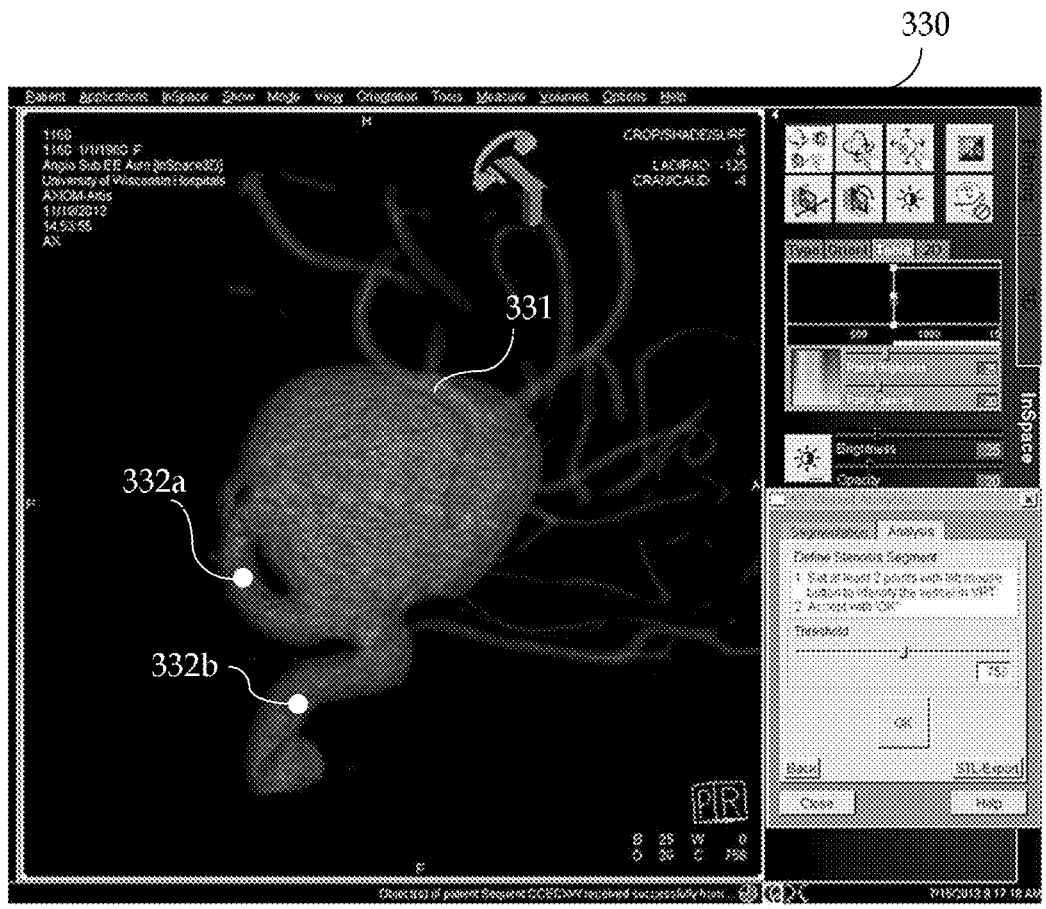
FIG. 3c shows an exemplary user interface for seed point positioning.

FIG. 3c shows an exemplary user interface 330 for seed point positioning. Two seed points 332a-b are placed by the user at the proximal and distal positions of the aneurysm 331. When the positioning of the seed points 332a-b is completed, automatic segmentation and analysis of the volume of interest may be performed based on the seed points 332a-b. If an error is returned, the user may place the seed points 332a-b in different positions and/or adjust the segmentation threshold higher or lower.

Returning to FIG. 2, at 206, evaluation unit 107 extracts the centerline of the volume of interest. The centerline of the volume of interest may be extracted semi-automatically or automatically. For example, skeletonization methods, such as distance transform or morphological thinning, may be applied.

At 208, evaluation unit 107 receives one or more user-selected points for interrogation. A user interface at, for example, workstation 103, may present a rendering of the volume of interest and enable the user to select one or more points along the centerline within the vessel segment for interrogation. The user may interrogate the vessel for changes in parameters (e.g., diameter, straightness) and/or blood dynamics measures (e.g., blood flow velocity, volumetric flow rate) by, for example, moving a pointer along the vessel and selecting one or more points. To evaluate quantitative measures of blood dynamics, the user may select a single point for differential volumetric flow rate or two points for volumetric flow rate between two points.

At 210, evaluation unit 107 determines one or more parameters and at least one blood dynamics measure associated with the one or more user-selected points. Parameters associated with the volume of interest may include, but are not limited to, the diameter along the vessel centerline and a straightness indicator. The straightness indicator aids the user in estimating turbulent flow likeliness at a given vessel segment point, and therefore points to the reliability of the calculated blood dynamics measure. Vessel straightness for a given vessel segment centerline point may be calculated by taking the directional vector along the vessel centerline at the user-selected point (or point of interest) and calculating the distance between the user-selected point (or point of interest) and where the normal of the directional vector intersects with the vessel wall in both proximal and distal directions. The resulting values may be normalized to the maximum value.

Quantitative measures of blood dynamics (e.g., flow velocity, volumetric flow rate between 2 points or differential volumetric flow rate at a single point) may be calculated based on the distance between two points and/or a measure of temporal distance. The vessel diameter (or cross-sectional area) at a given vessel centerline point may also be used in the calculation of, for example, volumetric flow rates or differential volumetric flow rate. Underlying a 4D DSA image dataset are time-contrast-concentration (TCC) curves for each voxel of a reconstructed vessel tree. Discrepancies between two TCC curves at two distant points may provide an impression on volumetric flow rate.

Figure 4:
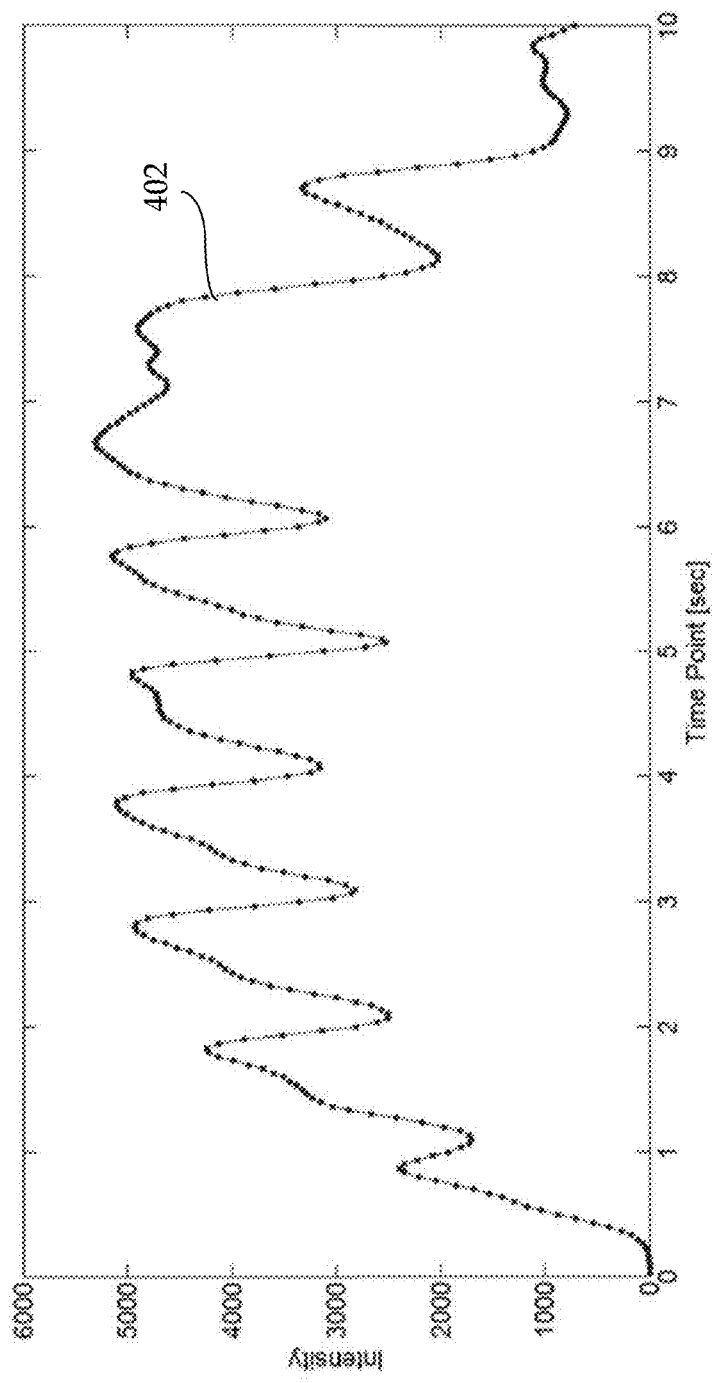
FIG. 4 shows an exemplary time-contrast-concentration (TCC) curve for a four-dimensional DSA vessel voxel.

FIG. 4 shows an exemplary time-contrast-concentration (TCC) curve 402 for a 4D DSA vessel voxel. The curve 402 represents the contrast inflow (first 2.5 sec), a stable phase (2.5 sec to 8 sec) and an outflow phase (8+ sec). Valleys in the stable phase represents less or non-opacified blood inflow from a cardiac systole; diluting the contrast results in less x-ray attenuation, while the peaks correspond to high contrast concentration due the cardiac rest period of the complete cardiac cycle and only little inflow of less or non-opacified blood.

Figure 5:
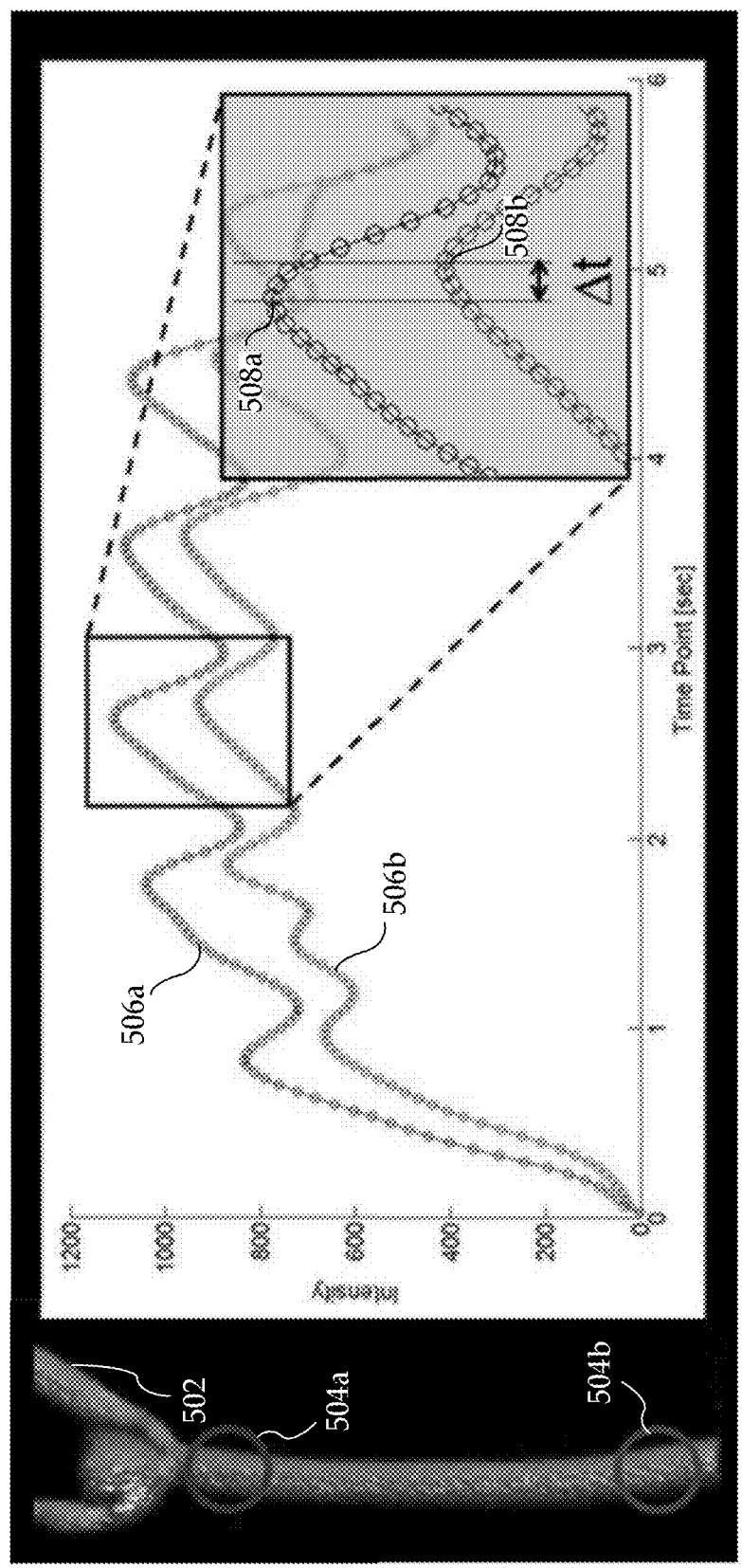
FIG. 5 shows an exemplary vascular segment with corresponding time-contrast-concentration (TCC) curves.

FIG. 5 shows an exemplary vascular segment (502) with corresponding time-contrast-concentration (TCC) curves (506a and 506b). The user has selected two points (504a and 504b) for measuring volumetric flow rate. The TCC curves (506a and 506b) correspond to these two user-selected points (504a and 504b). The determination of volumetric flow rate may make use of the distance (D) between the two points (504a and 504b), the vessel diameters (VD1 and VD2) at these points (504a and 504b), as well as a temporal difference ($\Delta t$) between these time curves (506a and 506bs). As shown, the temporal difference ($\Delta t$) may be derived by, for example, the time difference between maximum points (508a and 508b) of the TCC curves (506a and 506b). Other methods of deriving the temporal difference ($\Delta t$) may include, but are not limited to, optical flow methods or techniques based on the cross-correlation of the TCC curves. Such methods may be more robust (e.g., less sensitive to noise or slight motion). Knowing this information, the volumetric flow rate, Q, may be calculated as follows:

$$Q := \overline{Q} = \overline{A} \cdot \overline{v} \qquad (1)$$

wherein cross-sectional area $\overline{A}$ and flow velocity $\overline{v}$ may be described as follows:

$$Q = \frac{\pi}{4}\left(\frac{VD_1 + VD_2}{2}\right)^2 \frac{D}{\Delta t} \qquad (2)$$

While this implementation uses the average vessel diameter of the two points as the basis for the area, the average diameter of a set of vessel points between the points of interest may also be used.

Differential volumetric flow is the change in volumetric flow between adjoining vessels points, with respect to a user-selected location. For example, a point A has a flow velocity of n with respect to the user indicated point U, while a point B that adjoins point A has a flow velocity of m, with n>m. Volumetric flow rates may be calculated for each point in the set of vessel centerline points between A and U. The difference in volumetric flow rates between adjoining points in the set may also be calculated and displayed to the user as, for example, a color overlay on the vessel segment. By performing a point-by-point comparison, abrupt changes in flow may be highlighted, indicating potentially stenosed areas.

Returning to FIG. 2, at 212, evaluation unit 107 generates a visualization based on the one or more parameters and blood dynamics measures. The visualization may be presented via the user interface implemented at, for example, workstation 103. The user interface may enable the user to interrogate the volume of interest for parameters and blood dynamics information by selecting different points. When the user selects one or more different points, steps 208, 210 and 212 may be repeated to update the visualization.

Figure 6:
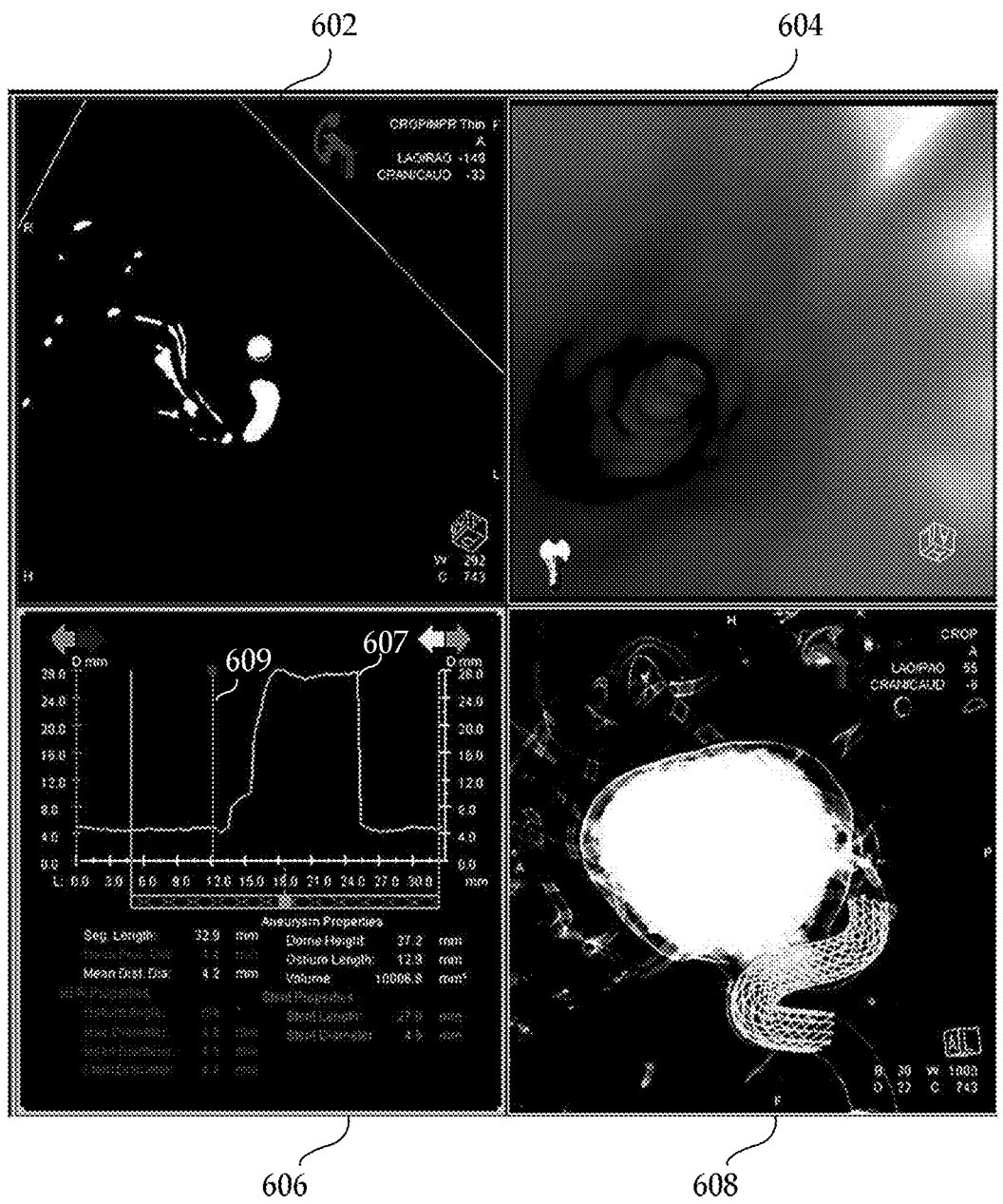
FIG. 6 shows an exemplary visualization.

FIG. 6 shows an exemplary visualization 600. The visualization 600 includes four exemplary views (602, 604, 606 and 608). The first view 602 shows the in-plane vessel dimensions (corresponding to the line 609 indicated in view 606). The second view 604 shows a volume rendering of an endoluminal view that corresponds to the red plane. The third view 606 shows a graph 607 of diameter D along the centerline of the vessel between user selected points. Additional information, such as vessel parameters (e.g., segment length, mean proximal diameter, mean distal diameter) and aneurysm dimensions (e.g., dome height, ostium length, volume) along the vessel centerline between the indicated points, may be displayed as text. If stent overlay is started, the stent dimensions may be displayed. The line 609 indicates the position along the vessel centerline as displayed in the second view 604. Although not shown, it should be appreciated that other vessel parameters (e.g., straightness indicator) and/or blood dynamics measures (e.g., flow velocity, volumetric flow rate), may also be displayed. The fourth view 608 shows a volume rendering of the vasculature and the overlaid stent.

One or more maps may be generated for a vascular segment representing a colorwash of values, such as contrast bolus time-of-arrival and contrast time-to-peak. The straightness indicator may also be displayed in a colorwash map (e.g., red indicating low vessel straightness and likely turbulent flow, green indicating high vessel straightness and unlikely turbulent flow). Volumetric flow rate may be represented as a single number when the user has indicated two points, or as a colorwash map for differential volumetric flow rates if the user indicated only one point. This colorwash map can potentially highlight flow break and speed-up points, indicating changes in flow behavior after, for example, an endovascular intervention.

Figure 7:
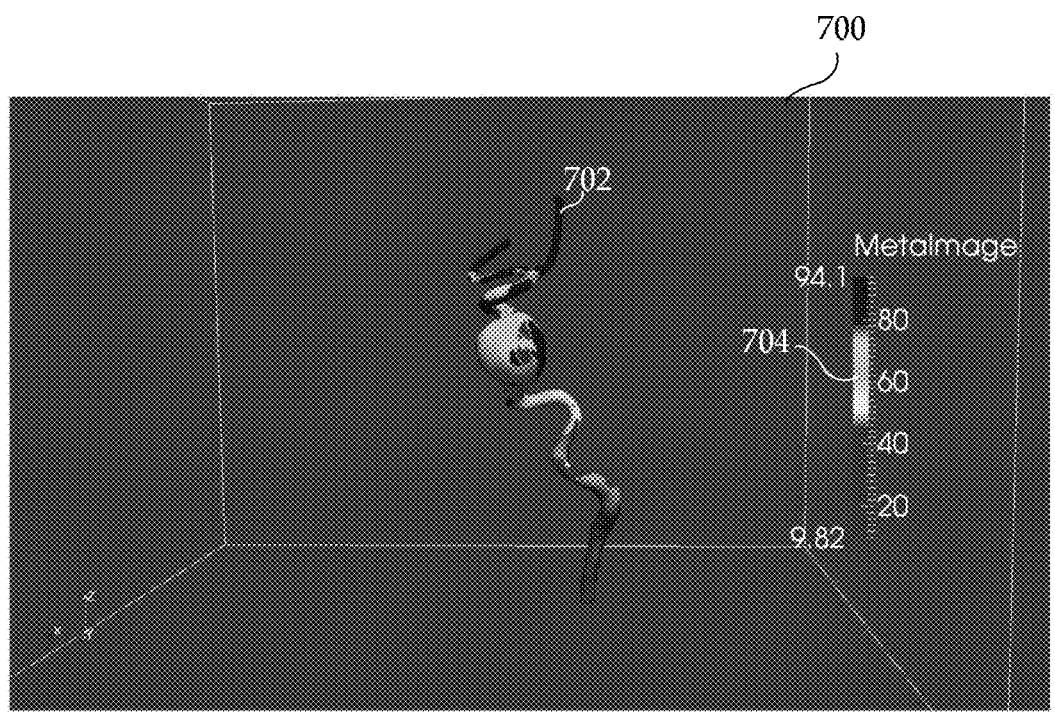
FIG. 7 shows an exemplary colorwash map.

FIG. 7 shows an exemplary colorwash map 700. Although the colorwash map 700 is shown as a grayscale map, it should be appreciated that other colors (e.g., blue, red, green, yellow) may also be used. Grayscale pixels are overlaid on the vascular segment 702 to represent contrast agent bolus arrival times (i.e., "BAT" or temporal quantities). The numbers along the grayscale bar 704 correspond to the numbers of the projection images within the contrast-enhanced rotational scan, with each projection image referring to a particular time point.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. One or more non-transitory computer-readable media embodying instructions executable by machine to perform operations for quantitative evaluation, comprising:
    delineating a volume of interest in a four-dimensional (4D) Digital Subtraction Angiography (DSA) dataset;
    extracting a centerline of the volume of interest;
    in response to receiving a single user-selected point along the centerline, determining a differential volumetric flow rate at the single user-selected point;
    in response to receiving at least two user-selected points along the centerline, determining a volumetric flow rate between the two user-selected points; and
    generating a visualization based on the differential volumetric flow rate or the volumetric flow rate between the two user-selected points.

2. The one or more non-transitory computer-readable media of claim 1 including further instructions executable by the machine to determine a straightness indicator that provides a measure of reliability of the differential volumetric flow rate or the volumetric flow rate between the two user-selected points.

3. A system for quantitative evaluation, comprising:
    a non-transitory memory device for storing computer readable program code; and
    a processor in communication with the memory device, the processor being operative with the computer readable program code to perform operations including
        delineating a volume of interest in a four-dimensional (4D) Digital Subtraction Angiography (DSA) dataset,
        extracting a centerline of the volume of interest,
        receiving one or more user-selected points along the centerline,
        determining at least one blood dynamics measure associated with the one or more user-selected points, and
        generating a visualization based on the blood dynamics measure.

4. The system of claim 3 wherein the processor is operative with the computer readable program code to generate the 4D DSA dataset by performing 4D reconstruction of time-varying image data.

5. The system of claim 3 wherein the processor is operative with the computer readable program code to delineate the volume of interest by performing thresholding.

6. The system of claim 3 wherein the processor is operative with the computer readable program code to receive one or more user-selected points via a user interface that presents a rendering of the volume of interest and enables a user to select the one or more user-selected points within the volume of interest.

7. The system of claim 3 wherein the processor is operative with the computer readable program code to determine the at least one blood dynamics measure associated with the one or more user-selected points by determining a differential volumetric flow rate at a single user-selected point.

8. The system of claim 3 wherein the processor is operative with the computer readable program code to determine the at least one blood dynamics measure associated with the one or more user-selected points by determining a volumetric flow rate between two user-selected points.

9. The system of claim 8 wherein the processor is operative with the computer readable program code to determine the volumetric flow rate between the two user-selected points based on a distance between the two user-selected points, diameters of the volume of interest at the two user-selected points and a temporal difference between time-contrast-concentration (TCC) curves corresponding to the two user-selected points.

10. The system of claim 9 wherein the processor is operative with the computer readable program code to determine the volumetric flow rate based on an average of the diameters of the volume of interest at the two user-selected points.

11. The system of claim 3 wherein the processor is operative with the computer readable program code to determine the at least one blood dynamics measure associated with the one or more user-selected points by determining a flow velocity.

12. The system of claim 3 wherein the processor is operative with the computer readable program code to further determine one or more parameters associated with the one or more user-selected points.

13. The system of claim 12 wherein the processor is operative with the computer readable program code to determine the one or more parameters by determining a straightness indicator that provides a measure of reliability of the blood dynamics measure.

14. The system of claim 13 wherein the processor is operative with the computer readable program code to determine the straightness indicator by calculating a directional vector along the centerline at the user-selected point and calculating a distance until a normal of the directional vector intersects with a wall of the vessel of interest in both proximal and distal directions.

15. The system of claim 3 wherein the processor is operative with the computer readable program code to generate the visualization by generating a colorwash map for differential volumetric flow rates that highlights flow break and speed-up points.

16. The system of claim 3 wherein the processor is operative with the computer readable program code to generate the visualization by displaying a number that indicates a volumetric flow rate.

17. The system of claim 3 wherein the processor is operative with the computer readable program code to generate the visualization by generating a colorwash map of a straightness indicator.

18. A method of quantitative evaluation, comprising:
delineating a volume of interest in a four-dimensional (4D) Digital Subtraction Angiography (DSA) dataset;
extracting a centerline of the volume of interest;
receiving one or more user-selected points along the centerline;
determining at least one blood dynamics measure associated with the one or more user-selected points; and
generating a visualization based on the blood dynamics measure.

19. The method of claim 18 wherein determining the at least one blood dynamics measure comprises determining differential volumetric flow rate at a single user-selected point.

20. The method of claim 18 wherein determining the at least one blood dynamics measure comprises determining volumetric flow rate between two user-selected points.

* * * * *